United States Patent
Callol

(10) Patent No.: US 6,585,757 B1
(45) Date of Patent: Jul. 1, 2003

(54) ENDOVASCULAR STENT WITH RADIOPAQUE SPINE

(75) Inventor: Joseph R. Callol, San Francisco, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/396,543

(22) Filed: Sep. 15, 1999

(51) Int. Cl.⁷ .................................................. A61F 2/06
(52) U.S. Cl. ..................................... 623/1.16; 623/1.34
(58) Field of Search ............................... 623/1.15, 1.16, 623/1.34, 23.7; 606/198

(56) References Cited

U.S. PATENT DOCUMENTS

| | | |
|---|---|---|
| 3,288,728 A | 11/1966 | Gorham |
| 3,839,743 A | 10/1974 | Schwarcz |
| 4,086,916 A | 5/1978 | Freeman et al. |
| 4,346,028 A | 8/1982 | Griffith |
| 4,633,873 A | 1/1987 | Dumican et al. |
| 4,656,083 A | 4/1987 | Hoffman et al. |
| 4,681,110 A | 7/1987 | Wiktor |
| 4,699,611 A | 10/1987 | Bowden |
| 4,718,907 A | 1/1988 | Karwoski et al. |
| 4,722,335 A | 2/1988 | Vilasi |
| 4,723,549 A | 2/1988 | Wholey et al. |
| 4,732,152 A | 3/1988 | Wallsten et al. |
| 4,733,665 A | 3/1988 | Palmaz |
| 4,739,762 A | 4/1988 | Palmaz |
| 4,768,507 A | 9/1988 | Fischell et al. |
| 4,776,337 A | 10/1988 | Palmaz |
| 4,816,339 A | 3/1989 | Tu et al. |
| 4,830,003 A | 5/1989 | Wolff et al. |
| 4,856,516 A | 8/1989 | Hillstead |
| 4,877,030 A | 10/1989 | Beck et al. |
| 4,878,906 A | 11/1989 | Lindemann et al. |
| 4,879,135 A | 11/1989 | Greco et al. |

(List continued on next page.)

FOREIGN PATENT DOCUMENTS

| | | |
|---|---|---|
| DE | A-44 07 079 | 9/1994 |
| EP | 0 380 668 B1 | 4/1989 |
| EP | 0 448 016 A | 9/1991 |
| EP | 0 517 075 A1 | 12/1992 |
| EP | 0 540 290 A2 | 5/1993 |
| EP | 0 565 251 A1 | 10/1993 |

(List continued on next page.)

OTHER PUBLICATIONS

Application for U.S. Letters Patent Ser. No. 08/233,046 filed Apr. 25, 1994.
Application for U.S. Letters Patent Ser. No. 08/564,936 (FWC of 08/233,046) filed Nov. 29, 1995.
Application for U.S. Letters Patent Ser. No. 08/234,547 filed Apr. 28, 1994.
Application for U.S. Letters Patent Ser. No. 08/559,931 (FWC of 08/234,547) filed Nov. 17, 1995.
Union Carbide Technology Letter, New Business Department—Parylene, Oct. 1973, No. 7 (8 pages).
Union Carbide, Electronic Materials, Parylene Products, Oct. 1973, No. 9 (23 pages).

(List continued on next page.)

Primary Examiner—Paul B. Prebilic
(74) Attorney, Agent, or Firm—Fulwider Patton Lee & Utecht, LLP

(57) ABSTRACT

A stent is formed from a series of radially aligned expandable rings. The rings are formed of a radio-transparent material that are linked by a radiopaque spine. A thin but very bright fluoroscopic image is thereby created, without compromising the strength of the stent. The small cross-section of the illuminated spine also serves to minimize interference with the image of the lesion when the stent is being positioned thereover. In the event galvanic corrosion causes the radiopaque spine to become detached from the radio-transparent ring elements, their expanded state precludes their shifting within the lumen. While the sandwiched position of the spine against the lumen wall prevents it from shifting as well.

11 Claims, 1 Drawing Sheet

U.S. PATENT DOCUMENTS

| | | |
|---|---|---|
| 4,886,062 A | 12/1989 | Wiktor |
| 4,913,141 A | 4/1990 | Hillstead |
| 4,943,346 A | 7/1990 | Mattelin |
| 4,994,071 A | 2/1991 | MacGregor |
| 4,994,298 A | 2/1991 | Yasuda |
| 5,019,090 A | 5/1991 | Pinchuk |
| 5,047,050 A | 9/1991 | Arpesani |
| 5,053,048 A | 10/1991 | Pinchuk |
| 5,059,211 A | 10/1991 | Stack et al. |
| 5,062,829 A | 11/1991 | Pryor et al. |
| 5,067,491 A | 11/1991 | Taylor, II et al. |
| 5,084,065 A | 1/1992 | Weldon et al. |
| 5,085,629 A | 2/1992 | Goldberg et al. |
| 5,102,417 A | 4/1992 | Palmaz |
| 5,104,404 A | 4/1992 | Wolff |
| 5,108,755 A | 4/1992 | Daniels et al. |
| 5,116,365 A | 5/1992 | Hillstead |
| 5,123,917 A | 6/1992 | Lee |
| 5,133,732 A | 7/1992 | Wiktor |
| 5,135,536 A | 8/1992 | Hillstead |
| 5,156,623 A | 10/1992 | Hakamatsuka et al. |
| 5,163,951 A | 11/1992 | Pinchuk et al. |
| 5,163,952 A | 11/1992 | Froix |
| 5,163,958 A | 11/1992 | Pinchuk |
| 5,192,311 A | 3/1993 | King et al. |
| 5,197,977 A | 3/1993 | Hoffman, Jr. et al. |
| 5,222,971 A | 6/1993 | Willard et al. |
| 5,226,913 A | 7/1993 | Pinchuk |
| 5,234,456 A | 8/1993 | Silvestrini |
| 5,234,457 A | 8/1993 | Andersen |
| 5,236,447 A | 8/1993 | Kubo et al. |
| 5,269,802 A | 12/1993 | Garber |
| 5,282,823 A | 2/1994 | Schwartz et al. |
| 5,282,860 A | 2/1994 | Matsuno et al. |
| 5,289,831 A | 3/1994 | Bosley |
| 5,290,271 A | 3/1994 | Jernberg |
| 5,304,200 A | 4/1994 | Spaulding |
| 5,306,286 A | 4/1994 | Stack et al. |
| 5,314,444 A | 5/1994 | Gianturco |
| 5,314,472 A | 5/1994 | Fontaine |
| 5,330,500 A | 7/1994 | Song |
| 5,342,348 A | 8/1994 | Kaplan |
| 5,342,621 A | 8/1994 | Eury |
| 5,356,433 A | 10/1994 | Rowland et al. |
| 5,360,443 A | 11/1994 | Barone et al. |
| 5,364,354 A | 11/1994 | Walker et al. |
| 5,383,927 A | 1/1995 | De Goicoechea et al. |
| 5,389,106 A | 2/1995 | Tower |
| 5,423,849 A | 6/1995 | Engelson et al. |
| 5,423,885 A | 6/1995 | Williams |
| 5,514,154 A | 5/1996 | Lau et al. |
| 5,562,728 A | 10/1996 | Lazarus et al. |
| 5,599,301 A | 2/1997 | Jacobs et al. |
| 5,607,442 A * | 3/1997 | Fischell et al. ............. 606/191 |
| 5,609,629 A | 3/1997 | Fearnot et al. |
| 5,628,787 A | 5/1997 | Mayer |
| 5,632,771 A * | 5/1997 | Boatman et al. ............... 623/1 |
| 5,637,113 A | 6/1997 | Tartaglia et al. |
| 5,649,951 A | 7/1997 | Davidson |
| 5,674,242 A | 10/1997 | Phan et al. |
| 5,741,327 A * | 4/1998 | Frantzen ........................ 623/1 |
| 5,858,556 A | 1/1999 | Eckert et al. |
| 6,113,628 A * | 9/2000 | Borghi ...................... 623/1.16 |
| 6,174,329 B1 * | 1/2001 | Callol et al. ............... 623/1.34 |
| 6,264,688 B1 * | 7/2001 | Herklotz et al. ........... 623/1.16 |
| 6,312,456 B1 * | 11/2001 | Kranz et al. ............... 623/1.13 |

FOREIGN PATENT DOCUMENTS

| | | |
|---|---|---|
| EP | A 0 578 998 | 1/1994 |
| EP | A 0 604 022 | 6/1994 |
| EP | A 0 621 017 | 10/1994 |
| EP | 0 679 372 A | 11/1995 |
| EP | 0 679 373 A | 11/1995 |
| FR | 2677872 A1 | 12/1992 |
| WO | WO 91/17789 | 11/1991 |
| WO | WO 93/06792 | 4/1993 |
| WO | WO 95/03010 | 2/1995 |
| WO | WO 95/29647 | 11/1995 |
| WO | WO 96/24393 | 8/1996 |

OTHER PUBLICATIONS

*Union Carbide Technology Letter*, May 1974, No. 11 (12 pages).

*Union Carbide Technology Letter*, Oct. 1975, No. 15 (13 pages).

Union Carbide, Electronic Materials, Parylene Products, Mar. 1976, No. 16 (4 pages).

Eskin, et al., *Growth of Cultured Calf Aortic Smooth Muscle Cells on Cardiovascular Prosthetic Materials*, J. Biomed. Mater. Res., vol. 10, pp. 113–122 (1976).

Loeb, et al., *Parylene as a Chronically Stable, Reproducible Microelectrode Insulator*, IEEE Transactions on Biomedical Engineering, Mar. 1977 (pp. 121–128).

Union Carbide, Electronic Materials, Parylene Products, Aug. 1977, No. 18 (7 pages).

Union Carbide, Electronic Materials, Parylene Products, Oct. 1977, No. 1 Revision 2 (7 pages).

Union Carbide, Electronic Materials, Parylene Products, Oct. 1977, No. 2 Revision 1 (9 pages).

Union Carbide, Electronic Materials, Parylene Products, Oct. 1977, No. 3 (21 pages).

Union Carbide, Electronic Materials, Parylene Products, Oct. 1977, No. 4 (13 pages).

Union Carbide, Electronic Materials, Parylene Products, Oct. 1977, No. 6 (12 pages).

Union Carbide, Electronic Materials, Parylene Products, Oct. 1977, No. 7 Revision 1 (8 pages).

Union Carbide, Electronic Materials, Parylene Products, Oct. 1977, No. 8 Edited (19 pages).

Union Carbide, Electronic Materials, Parylene Products, Oct. 1977, No. 10 (50 pages).

Union Carbide, Electronic Materials, Parylene Products, Oct. 1977, No. 11 (12 pages).

Union Carbide, Electronic Materials, Parylene Products, Oct. 1977, No. 12, Revision 1 (6 pages).

Union Carbide, Electronic Materials, Parylene Products, Oct. 1977, No. 13, Revision 1 (7 pages).

Union Carbide, Electronic Materials, Parylene Products, Oct. 1977, No. 14. Revision 1 (11 pages).

Union Carbide, Electronic Materials, Parylene Products, Oct. 1977, No. 15, Revision 1 (8 pages).

Union Carbide, Electronic Materials, Parylene Products, Oct. 1977, No. 17, Revision 1 (11 pages).

*ISEEE Transactions on Biomedical Engineering*, vol. BME–27, No. 11, Nov. 1980 (5 pages).

Sadhir, et al., The Adhesion of Glow–Discharge Polymers, Silastic and Parylene to Implantable Platinum Electrodes: Results of Tensile Pull Tests After Exposure to Isotonic Sodium Chloride, 10/81, vol. 2, Biomaterials (pp. 239–243).

Hahn, et al., *Glow Discharge Polymers as Coatings for Implanted Devices*, John M. Dalton Research Center, University of Missouri–Columbia and the Graduate Center for Materials Research, 1981 (pp. 109–113).

*Union Carbide, Electronic Materials, Parylene Products,* Jan. 18, 1982, No. 5, Revision 4 (17 pages).

Hahn, et al., Biocompatibility of Glow–Discharge–Polymerized Films and Vacuum–Deposited Parylene, *Journal of Applied Polymer Science: Applied Polymer Symposium* 38, 55–64 (1984).

Casper, et al., Fiber–Reinforced Absorbable Composite for Orthopedic Surgery, *Polymeric Materials Science and Engineering,* Proceedings of ACS Division of Polymeric Materials: Science & Engineering, vol. 53, Fall Mtg. 1985.

Kelley, et al., Totally Reformable High–Strength Composite Material, *Advances in Biomedical Polymers,* Edited by Charles G. Gebelein (1987).

Yuen, et al., *Tissue Response to Potential Neuroprosthetic Materials Implanted Subdurally,* Biomaterials, Mar. 1987, vol. 8 (pp. 57–62).

Nichols, et al., *Electrical Insulation of Implantable Devices by Composite Polymer Coatings,* Dalton Research Center, University of Missouri, 1987.

Schmidt, et al., *long–Term Implants of Parylene–C Coated Microelectrodes,* Medical & Biological Engineering & Computing, Jan. 1988 (pp. 96–101).

Olson, *Parylene, a Biostable Coating for Medical Applications,* for NOVA TRAN Parylene Coating Services (Jul. 25, 1988; Nov. 14, 1988).

Beach, et al., Xylylene Polymers, *Encyclopedia of Polymer Science and Engineering,* vol. 17, Second Edition, pp. 990–1025, 1989.

Muller, et al., Advances in Coronary Angioplasty: Endovascular Stents, *Coronary Artery Disease,* Jul./Aug. 1990, vol. 1, No. 4.

Loh et al., *Plasma Enhanced Parylene Deposition,* Antec, pp. 1099–11033, 1991.

Wong, M.D., et al., An Update on Coronary Stents, *Cardio,* Feb. 1992.

Gebelein, et al., *Biomedical and Dental Applications of Polymers,* Polymer Science and Technology, vol. 14 (no date) (pp. 143–161).

*The Parylene Press*(A Publication of Specialty Coating Systems, Inc.) Winter 1992 (7 pages).

Charlson, et al., *Temperature Selective Deposition of Parylene–C,* IEEE Transactions on Biomedical Engineering, vol. 39, No. 2, Feb. 1992 (pp. 202–206).

Bull: *Parylene Coating for Medical Applications,* Medical Product Manufacturing News, Mar. 1993 (2 pages).

*The Parylene Press* (A Pulbication of Specialty Coating Systems, Inc.), Spring 1993 (6 pages).

*The Parylene Press* (A Publication of Specialty Coating Systems, Inc.), Summer 1993 (4 pages).

*Information Regarding Parylene–C Coating for ACS Metal Stent,* In–House Memorandum from Ed Newton to Joe Callol, et al., Oct. 15, 1993 attaching *Parylene, A Biostable Coating for Medical Applications* by Roger Olson.

Moody: *Vacuum Coating Ultrasonic Transducers,* Sensors, Dec. 1993 (1 page).

*Union Carbide A–174 Silane,* Sales Brochure, Union Carbide Adhesion Promoters, Jan. 1968 (5 pages).

*Typical Parylene Properties,* Printout, Para Tech Coating Company; *Lab Top® Parylene Deposition System Model 3000,* Sales Brochure, Para Tech Coating Company (7 pages).

*Parylene Environmentally Compatible Conformal Coatings for Electronic Components Assemblies and Precision Parts,* Brochure, Union Carbide Electronics Division (14 pages).

*Parylene and Nova Tran™ Parylene Coating Services for Unmatched Conformal Coating Performance,* Brochure, Union Carbide Specialty Coating Systems (21 pages).

*Repair and Recoating of Parylene Coated Printed Circuit Boards,* Brochure, Union Carbide Specialty Coating Systems (15 pages).

*Nova Tran™ Custom Coating Services, Parylene Conformal Coating,* Brochure, Union Carbide (8 pages).

*Parylene, a Biostable Coating for Medical Applications,* Brochure, Union Carbide Specialty Coating Systems (6 pages).

Application of U.S. Letters Patent Ser. No. 09/298,263, filed Apr. 22, 1999.

* cited by examiner

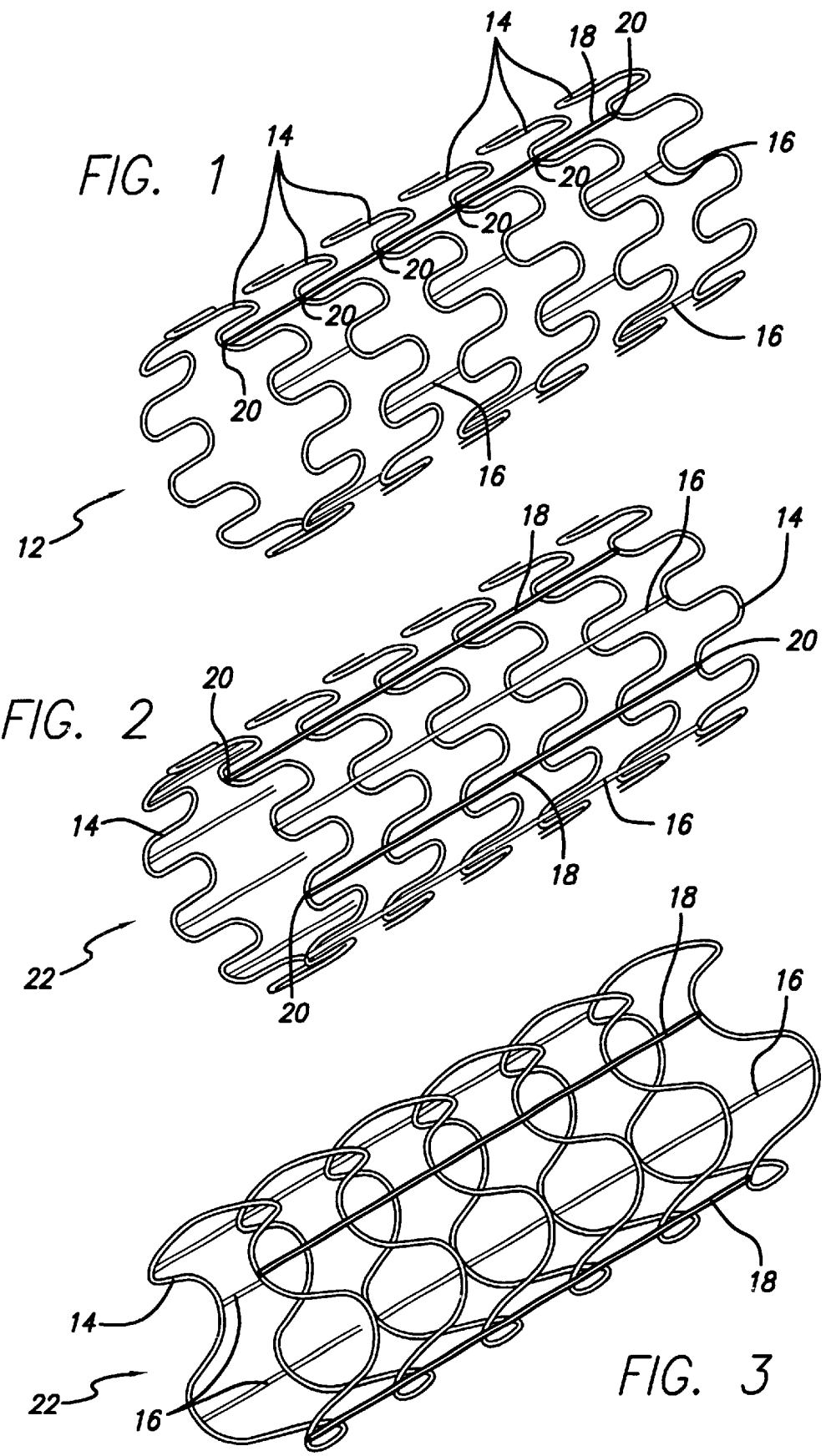

ENDOVASCULAR STENT WITH RADIOPAQUE SPINE

BACKGROUND OF THE INVENTION

This invention generally relates to endoprosthesis devices, most often referred to as stents, and more particularly pertains to the radiopaque marking of such devices.

Stents are useful in the treatment of atherosclerotic stenosis in blood vessels and are generally tubular shaped devices which function to hold open a segment of a blood vessel or other anatomical lumen. They are particularly suitable for use in supporting and holding back a dissected arterial lining which could otherwise occlude the fluid passageway therethrough.

In order to accomplish precise placement of stents, various means are employed to identify the position of the stent within a blood vessel. One means frequently described for accomplishing precise placement of a stent is the attachment of small radiopaque markers to the stent so that through the use of fluoroscopy, the position of the stent within a blood vessel can be identified. Once the stent with its radiopaque markers has been implanted, subsequent checkups of the treated segment are easily performed since the markers remain visible under fluoroscopic illumination.

Conventional radiopaque markers, however, have a number of limitations. Upon attachment to a stent, conventional radiopaque markers may project from the surface of the stent, thereby comprising a departure from the ideal profile of the stent. Such conventional radiopaque markers protrude from the walls of the stent and depending upon their location upon the stent, may either project inwardly to disrupt blood flow or outwardly to traumatize the walls of the blood vessel. In addition, conventional radiopaque markers have the disadvantage in that their attachment to the stent can be tedious and imprecise. Moreover, the configuration of many heretofore known markers fails to provide a precise indication of the location and position of the stent. Finally, the galvanic corrosion that might result from the contact of two disparate metals, i.e., the metal used in the construction of the stent and the radiopaque metal of the marker could eventually cause the marker to become separated from the stent which could be problematic should the marker be swept downstream.

Other conventional radiopaque markers restrict the expansion capabilities of an expandable stent by adding rigidity to the stent in areas designated for stent deformation. In other cases, the stents are formed wholly of radiopaque material, such as tantalum, that is highly effective for use in identifying the location of a stent within a vessel, but fluoroscopically illuminates so brightly so as to obscure proper visibility of the blood vessel lesion, thereby impairing the ability to repair the lesion. Finally, conventional radiopaque markers do not generally, under fluoroscopy, provide the operator with means to accurately access the position of the entire length of the stent.

Stents have also been previously marked by plating selected portions thereof with a radiopaque material. An advantageously selected pattern of plated areas would theoretically allow the position, length and diameter of the stent to be discerned. However, due to the minimal thickness of the plating, only an extremely faint fluoroscopic image can be generated which may ultimately limit its utility. Plating may also lead to flaking of the plated material which will embolize and result in undesirable conditions.

To overcome the problems and limitations associated with stents having conventional radiopaque markers, or plated markers, it would be desirable to employ radiopaque markers or markings that do not limit or otherwise interfere in the expansion capabilities of an expandable stent, nor alter the profile of the stent, that are clearly visible, that provide means for visualizing the entire length of the stent, that do not obscure the blood vessel lesion being repaired and that are not detrimentally affected by galvanic corrosion.

SUMMARY OF THE INVENTION

The present invention provides for the radiopaque marking of a stent so as to effectively identify the position of such stent, both while fitted to the delivery device as well as upon implantation within a blood vessel, without inordinately obscuring the lesion being repaired. While the marking may form an integral part of a stent, it does not in any way limit the expansion capabilities of the stent. Furthermore, the marking is not adversely affected by galvanic corrosion. The radiopaque marking of the present invention may be adapted to stents having various geometric shapes and that are constructed of any of various materials.

In a preferred embodiment, the stent of the present invention is of wire construction wherein a plurality of shaped wire rings are axially aligned and appropriately linked. This type of stent is well known in the art and offers significant advantages in terms of expandability, radial strength, longitudinal flexibility, and longitudinal stability during expansion. However, no radiopaque materials are known that satisfy the strength and biocompatibility requirements of such application. In order to render such stents fluoroscopically visible in accordance with the present invention, one or more spines of the stent are wholly formed of a radiopaque material. Such construction provides all of the advantages set forth above. Because the spine is wholly constructed of highly radiopaque material, it creates a brilliant image when fluoroscopically illuminated. Its presence along the entire length of the stent serves to unequivocally reveal the position and orientation of the stent. At the same time, the relatively small cross-section of the radiopaque spine serves to minimize the width of the image and therefore only minimally interferes with the visibility of a lesion adjacent thereto.

Additionally, because the spine runs longitudinally along the length of the stent, it does not participate in nor interfere with the deployment of the stent in which all deformation is limited to the radial expansion of the individual rings. Moreover, expansion causes the expanding rings to engage the vessel walls and thus causes the radiopaque spine to become sandwiched therebetween. Should galvanic corrosion cause the spine to become detached from any or all of the expanding rings to which it was originally attached, the spine will continue to be held in place by the radially outwardly directed forces of the expanded rings. Similarly, because each of the rings firmly engages the vessel walls and because the rings may be interconnected by one or more non-galvanically susceptible spines formed of radio transparent material, there is no danger of the rings becoming displaced. Additionally, because the radiopaque spine as well as the radiotransparent spines are located on the exterior of the rings, the flow of blood through the rings is not disrupted thereby and thus platelet activation and thrombosis formation is less likely. This in turn promotes healing and enhances the growth and attachment of endothelium while suppressing the proliferation of growth of smooth muscle cells and excess neointima in the vessels. The minimal thickness of the spines prevents the vessel walls from being traumatized.

The stent may be constructed using any of a variety of techniques including fabricating the series of expanding rings and then linking selected or all of the rings to the radiopaque spine. Any of various methods may be employed to attach the radiopaque spine to the radiotransparent rings.

These and other features and advantages of the present invention will become apparent from the following detailed description of a preferred embodiments which, taken in conjunction with the accompanying drawings, illustrate by way of example the principles of the invention.

BRIEF DESCRIPTION OF THE DRAWINGS

FIG. 1 is a perspective view of a stent of the present invention.

FIG. 2 is a perspective view of an alternative embodiment stent of the present invention.

FIG. 3 is a perspective view of the stent shown in FIG. 2 in its expanded state.

DETAILED DESCRIPTION OF THE PREFERRED EMBODIMENTS

The stent of the present invention includes a radiopaque marking that renders the stent's position clearly visible while nonetheless allowing the treatment site to be visualized. This enables the position of the stent to be monitored as it is being advanced through the vasculature by the delivery catheter, and allows the stent to be very precisely positioned relative to the target site. The permanent marking additionally allows the stent's presence to be easily detected or verified at any time thereafter.

FIG. 1 illustrates a preferred embodiment representative of the present invention. The stent 12 is of wire construction wherein a series of rings are axially aligned and joined to one another. The undulating configuration allows the rings to be radially expanded such that the stent device can be introduced into the vasculature and advanced therethrough while in a relatively small diameter, low profile state and then expanded into a relatively large diameter, deployed state to provide support to a lumen. Expansion can be achieved by for example the inflation of an expandable balloon about which the stent is carried as it is advanced into place.

As is shown in FIG. 1, the individual rings 14 are joined by spines 16,18 that are longitudinally oriented along the entire stent. While the individual rings 14 of the stent and spines 16 are constructed of a radio-transparent material such as stainless steel, Nitinol, or titanium, spine 18 is constructed of a highly radiopaque material such as platinum-iridium, platinum, gold, or tantalum. The particular embodiment illustrated employs a single radiopaque spine 18. Additionally, in this particular embodiment, the radiopaque spine is joined to each and every ring 14 at points 20. It is noted that stainless steel is essentially radio-transparent when small diameter wire is used, thus stent rings 14 and spine 18 can be made from stainless steel as well.

The rings 14 may all be fabricated separately and then attached to the spines 16, 18 by any of various well known means such as by welding, laser welding, resistance welding, diffusion bonding, mechanical means or with the use of adhesives such as epoxies. The spines may have a round rectangular or a flat cross-section. Round wire spines have dimensions on the order of 0.002–0.010 inch in diameter. Rectangular or flat ribbon utilized as spine material is 0.003–0.010 inch wide and 0.001–0.005 inch thick.

FIG. 2. illustrates an alternative embodiment stent 22 in which more than one, and specifically two radiopaque spines 18 are employed. Additionally, such spines are joined 20 to only the most proximal and most distal rings 14. Other combinations of the number of radiopaque spines and the number of attachment points 20 are within the scope of the present invention.

FIG. 3 illustrates the stent shown in FIG. 2 in its expanded state. Each of the radio transparent rings 14, has undergone deformation to facilitate an increase in the diameter of the stent. The radiopaque spines 18, along with the radio-transparent spines 16 are not in any way been affected by and do not participate in the expansion. Upon expansion, the spines 16,18 continue to hold the expanded rings in place relative to one another.

The material used in the construction of the rings 14 and radiotransparent spines 16 is selected for its structural characteristics such as radial strength, expansion capability, longitudinal flexibility as well as its biocompatibility. In addition, so as not to obstruct the image of a lesion to be treated, such material must also be radio-transparent. The material used in the construction of the marker spines 18 is selected for its radiopacity and biocompatibility.

In use, the stent is first tightly crimped about the expandable balloon element of a balloon catheter while the stent is in its collapsed state. In such state, the position of the stent relative to the delivery device is visible as fluoroscopic illumination causes the radiopaque spine or spines of the stent as well as radiopaque markers positioned on the delivery device to be clearly visible. The position of the spine image or images relative the image or images of any markings on the delivery device serve to indicate the position of the stent on the delivery device.

As the stent carrying delivery catheter is inserted into and advanced through the vasculature, the position of the stent relative the delivery device can be continually monitored. Any shifting of the stent relative to the catheter can be immediately spotted and the appropriate remedial action taken. The radiopacity of the spine or, the spines 18 of the stent also enhances the visibility of the stent/delivery catheter combination to enable its progress through the vasculature to be followed.

As the deployment site is approached, the position of the stent is fine tuned by juxtaposing the illuminated spine or spines within the lesion. While the use of highly radiopaque material in the construction of such spines causes them to illuminate very brightly, its visibility as straight and thin lines ensures that its image does not obscure or only minimally obscures the substantially fainter image of a lesion when positioned therein or directly adjacent thereto. The stent can therefore be precisely centered within the lesion.

The fact that a stent has been implanted is readily evident during a radiological examination of the patient later in life as the bright image generated by a radiopaque spine can not be over looked. Additionally, because the rings are expanded against the vessel walls, and because they may be interconnected by radio-transparent spines, they remain in place even if galvanic corrosion should cause one or more of the rings to become separated from the radiopaque spine. Similarly, because the radiopaque spine is sandwiched between the expanded rings and the lumen walls, the spine also stays in place even if galvanic corrosion causes all rings to become disjoined from such spine. As a result, the position of the stent continues to be clearly discernable and the possibility of a component thereof from being washed downstream is effectively eliminated.

While a particular form of the invention has been illustrated and described, it will also be apparent to those skilled in the art that various modifications can be made without departing from the spirit and scope of the invention. Accordingly, it is not intended that the invention be limited except by the appended claims.

What is claimed is:

1. An intravascular stent having a generally cylindrical shape, comprising:
    a series of rings formed only of radio-transparent material and configured so as to be expandable; and
    a spine, longitudinally oriented and continuously extending along the entire length of said stent, the entire length of said spine formed of radiopaque material and said spine directly connected to at least two of said rings.

2. The stent of claim 1, wherein said spine of radiopaque material is directly connected to all of said rings.

3. The stent of claim 1, further comprising a second spine, longitudinally oriented along said stent, formed of radiopaque material and directly connected to at least two of said rings.

4. The stent of claim 3, wherein all said spines of radiopaque material are each directly connected to all of said rings.

5. The stent of claim 1, further comprising an additional spine, longitudinally oriented along said stent, formed of radio-transparent material and directly connected to each of said rings.

6. The stent of claim 1, wherein said radio-transparent material is selected from the group comprising stainless steel, titanium, and Nitinol and said radiopaque material is selected from the group comprising iridium-platinum, platinum, tantalum and gold.

7. The stent of claim 1, wherein each said ring comprises a wire structure.

8. The stent of claim 7, wherein said wire is of round cross-section.

9. The stent of claim 7, wherein said wire is of rectangular cross-section.

10. The stent of claim 1, wherein said radiopaque material and said radio-transparent materials are connected by welding.

11. An intravascular stent having a generally cylindrical shape, comprising:
    a series of rings formed only of radio-transparent material and configured so as to be expandable;
    a first spine, longitudinally oriented and continuously extending along the entire length of said stent, formed of radiopaque material and directly connected to at least two of said rings; and
    a second spine, longitudinally oriented along said stent, formed of radio-transparent material and directly connected to each of said rings.

* * * * *